(12) United States Patent
Edens et al.

(10) Patent No.: US 8,197,537 B2
(45) Date of Patent: Jun. 12, 2012

(54) IMPLANTABLE TEXTILE PROSTHESES HAVING PTFE COLD DRAWN YARNS

(75) Inventors: Wesley I. Edens, Wayne, NJ (US); Charles B. Hebert, Excelsior, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1490 days.

(21) Appl. No.: 11/499,475

(22) Filed: Aug. 4, 2006

(65) Prior Publication Data
US 2006/0271157 A1 Nov. 30, 2006

Related U.S. Application Data

(63) Continuation of application No. 10/132,367, filed on Apr. 25, 2002, now Pat. No. 7,105,021.

(51) Int. Cl.
*A61F 2/06* (2006.01)
(52) U.S. Cl. .................. 623/1.5; 623/1.51; 623/1.54
(58) Field of Classification Search .................. None
See application file for complete search history.

(56) References Cited

U.S. PATENT DOCUMENTS

| | | | |
|---|---|---|---|
| 3,582,418 A | 6/1971 | Schuur | |
| 3,966,867 A | 6/1976 | Munting | |
| 4,003,974 A | 1/1977 | Chantry et al. | |
| 4,064,214 A | 12/1977 | FitzGerald | |
| 4,414,169 A | 11/1983 | McClary | |
| 4,482,516 A | 11/1984 | Bowman et al. | |
| 4,491,657 A | 1/1985 | Saito et al. | |
| 4,869,958 A | 9/1989 | Murase et al. | |
| 4,897,902 A * | 2/1990 | Kavesh et al. | ........... 28/166 |
| 4,965,342 A | 10/1990 | Vandenberg et al. | |
| 5,098,625 A | 3/1992 | Huang et al. | |
| 5,238,740 A | 8/1993 | Simons et al. | |
| 5,286,324 A | 2/1994 | Kawai et al. | |
| 5,340,517 A | 8/1994 | Koschinek et al. | |
| 5,387,300 A | 2/1995 | Kitamura | |
| 5,562,987 A | 10/1996 | Shimizu | |
| 5,607,478 A * | 3/1997 | Lentz et al. | ........... 623/23.69 |
| 5,670,161 A | 9/1997 | Healy et al. | |
| 5,686,033 A | 11/1997 | Shimizu | |
| 5,718,159 A | 2/1998 | Thompson | |
| 5,741,332 A * | 4/1998 | Schmitt | ........... 623/23.64 |
| 5,758,562 A | 6/1998 | Thompson | |
| RE35,972 E | 11/1998 | Cuculo et al. | |
| 5,891,191 A | 4/1999 | Stinson | |
| 5,928,279 A | 7/1999 | Shannon et al. | |

(Continued)

FOREIGN PATENT DOCUMENTS
EP 0804909 A2 11/1997
(Continued)

*Primary Examiner* — Thomas J Sweet
*Assistant Examiner* — Christopher D Prone
(74) *Attorney, Agent, or Firm* — Vidas, Arrett & Steinkraus, P.A.

(57) ABSTRACT

The present invention provides an implantable prosthesis and more specifically, an implantable tubular textile prosthesis comprising a biocompatible fabric having inner and outer surfaces and first and second ends; the fabric having a textile construction comprising cold drawn PTFE yarns having a substantially uniform denier and high molecular orientation. Use of cold drawn PTFE yarns result in implantable prostheses that have excellent abrasion resistance, strength and lubricity properties. Useful textile constructions include weaves, knits, braids, filament windings, spun windings and combinations thereof. The prostheses of the present invention are lubricious and have characteristics that closely resemble the properties of a natural body lumen.

20 Claims, 8 Drawing Sheets

| U.S. PATENT DOCUMENTS | | | | FOREIGN PATENT DOCUMENTS | | |
|---|---|---|---|---|---|---|
| 6,015,616 A | 1/2000 | Simons et al. | | EP | 0855170 A2 | 7/1998 |
| 6,068,805 A | 5/2000 | Lockridge et al. | | GB | 2347861 A | 9/2000 |
| 6,071,452 A | 6/2000 | Kelmartin, Jr. et al. | | JP | 291210 | 3/1990 |
| 6,074,084 A | 6/2000 | Kolossow | | * cited by examiner | | |
| 6,342,068 B1 | 1/2002 | Thompson | | | | |

FIG 3A  FIG 3B

IMPLANTABLE TEXTILE PROSTHESES HAVING PTFE COLD DRAWN YARNS

CROSS REFERENCE TO RELATED APPLICATIONS

This application is a continuation of U.S. patent application Ser. No. 10/132,367, filed Apr. 25, 2002, issued Sep. 12, 2006 as U.S. Pat. No. 7,105,021.

FIELD OF THE INVENTION

The present invention relates to an implantable textile prosthesis. More particularly, the present invention relates to an implantable textile prosthesis with substantially improved lubricious properties having cold drawn polytetrafluoroethylene (PTFE) yarns therein.

BACKGROUND OF RELATED TECHNOLOGY

Vascular grafts are commonly used as soft tissue prostheses to replace or repair damaged or diseased veins and arteries. Conventional textile implantable prostheses are manufactured using yarns made of biocompatible and biostable material. To maximize the effectiveness of prostheses, it is desirable that the prostheses have characteristics that closely resemble that of the natural body lumen. In particular, prostheses desirably exhibit long term wear and kink resistance. Typically, the yarns used in these types of textile constructions are subjected to strenuous conditions, such as constant rubbing against a stent during pulsation of blood. Such abrasive forces can result in weakening of conventional textile prosthesis made with polyethylene terephthalate (PET) yarns, which can result in loss of structural integrity, and in extreme cases graft failure. Thus, there is a need for more durable and lubricious yarns that are capable of being incorporated into vascular prostheses.

PTFE is used in numerous demanding applications due to its excellent physical properties, which include excellent high and low temperature performance, chemical resistance and lubricious properties. PTFE is particularly useful in medical devices such as vascular prostheses. Use of PTFE yarns for textile vascular prostheses has been limited because finished PTFE yarns suitable for use in medical devices are often not commercially available to medical device manufacturers. Unfinished PTFE yarns that are available, however, typically do not possess the physical characteristics necessary for such medical device uses, such as sufficient orientation, i.e. molecular alignment of the fibers, and the requisite uniform linear density. This creates problems when processing such yarns into a textile prosthesis. For instance, unfinished yarns may accumulate in the machine during the textile prosthesis manufacturing process or stretch to create a non-uniform prosthesis. Additionally, problems may occur when such prostheses having unfinished PTFE yarns therein are placed in a body lumen because such yarns may unexpectedly and undesirably stretch. Thus, the prostheses will not perform in a consistent and predictable manner. As such, these yarns are not suitable for use in medical devices without further processing.

Conventional means to finish PTFE yarns typically involve a heat drawing process. Heat drawing results in yarns with good orientation and uniform linear density which when incorporated into a textile vascular prosthesis exhibit predictable and consistent behavior, both in the textile manufacturing process and in vivo. However, it may be difficult to control and maintain the elevated temperature that is necessary for heat drawing and it may be expensive to obtain heat drawing equipment. Thus, conventional methods for drawing yarns suitable for use in implantable textile prostheses are less than satisfactory.

Accordingly, it is desirable to provide textile prostheses with improved lubricious properties comprising cold drawn PTFE yarns having have a uniform linear density and a highly oriented molecular structure and drawn using a convenient and inexpensive cold drawing process.

SUMMARY OF THE INVENTION

The present invention provides for implantable textile prostheses having PTFE yarn, which are suitable for medical device use. More particularly, the present invention provides for textile prostheses having highly lubricious cold drawn PTFE yarns that have a highly oriented molecular structure and a uniform linear density. Cold drawn PTFE yarn exhibits enhanced handling characteristics, which minimize the tendency of yarns to fold back and accumulate during a braiding process. Yarns useful for braided grafts are desirably single or two-ply 225 denier, 30 filaments with 0.5 to 10 twists per inch inserted.

An implantable textile prosthesis comprising a biocompatible fabric having inner and outer surfaces and first and second ends; the fabric having a textile construction including cold drawn PTFE yarns having a substantially uniform denier and high molecular orientation. Useful textile constructions include weaves, knits, braids, filament windings, spun windings and combinations thereof.

Another embodiment of the present invention provides a braided textile prosthesis with enhanced lubricity, biocompatibility and chemical resistance properties having a braided, tubular shaped fabric having inner and outer surfaces and first and second ends; the fabric having cold drawn PTFE yarns having a substantially uniform linear density and high molecular orientation.

Yet another embodiment of the present invention provides for a method for making a lubricious biocompatible tubular prosthesis including providing a fabric having an inner and outer surface and first and second ends, the fabric having a plurality of polymeric filaments comprising cold drawn PTFE yarns having a substantially uniform linear density and a highly oriented molecular structure; selecting a textile construction pattern; and forming the prosthesis in accordance with a textile construction pattern.

BRIEF DESCRIPTION OF THE DRAWINGS

FIG. 3A is a schematic of a diamond braid useful in the present invention.

FIG. 3B is a schematic of a regular braid useful in the present invention.

DETAILED DESCRIPTION OF THE INVENTION

Figure 1:
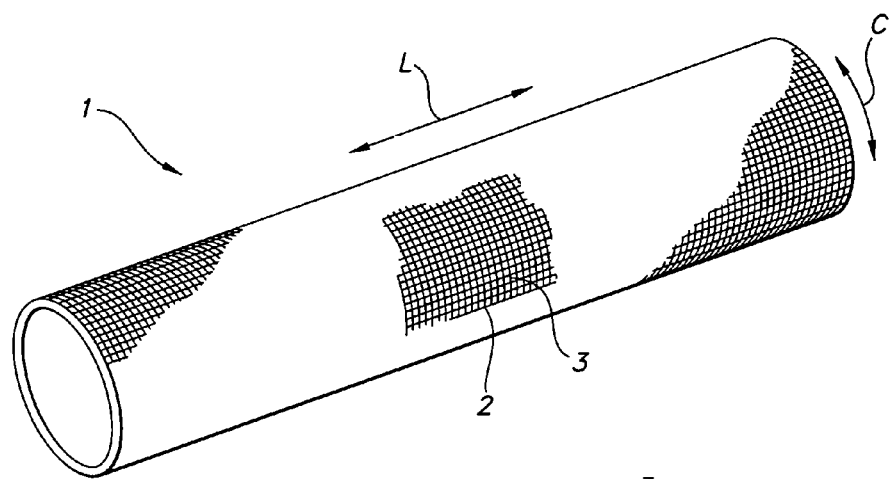
FIG. 1 is a perspective view of a tubular woven tubular prosthesis useful in the present invention.

In accordance with the present invention, there is provided an implantable textile prosthesis and more specifically, an implantable textile prosthesis having cold drawn PTFE yarns with a substantially uniform linear density and a highly oriented molecular structure. Use of cold drawn PTFE yarns result in implantable prostheses that have excellent abrasion resistance, strength and lubricity properties. The prostheses of the present invention have characteristics that closely resemble the properties of a natural body lumen.

Cold drawn PTFE yarns increase the durability of prostheses, which may reduce the need for physicians to routinely remove, repair and replace vascular prostheses that have been implanted. An advantage of cold drawn PTFE yarns is that they are convenient and easy to produce.

The present invention contemplates implantable prostheses, such as endovascular grafts, balloon catheters, meshes, vascular patches, hernia plugs, stent-graft composites, blood filters and the like. One embodiment of the present invention contemplates a tubular implantable prosthesis. Examples of prostheses that may require a tubular design include intraluminal prostheses, endovascular grafts, radially deformable support components, such as radially deformable stents.

Stent-graft composite devices are also contemplated having self-expanding stents and balloon expandable stents. Self-expanding stents include those that have a spring-like action which causes the stent to radially distend (expand and contract) or stents which expand due to the memory properties of the stent material for a particular configuration at a certain temperature. Stent-graft composite devices often pulsate in the body in accordance with the passage of blood. Such movement may cause abrasion of the graft by the metal stent, leading to a weakening of the integrity of the prosthesis. Fabrics made from cold drawn PTFE yarns perform well in conjunction with stents due to the durability and abrasion resistance of the cold drawn PTFE yarn.

The linear density of the yarn used in the prosthesis is selected to meet specific properties desired for the prosthesis, such as porosity, flexibility and compliance. Denier is a unit of measure to represent the linear density of the yarn. In particular, denier is the weight of the yarn in grams per 9000 meters of yarn. Yarns useful in the inventive prostheses have a denier range from about 40 to about 400, depending on the specific type of vascular graft desired. Yarns desirably have a denier from about 100 to about 300. Yarns may be flat, twisted, textured or pre-shrunk. The yarns may be multifilament, monofilament or spun type. Desirably, multifilaments are used, however, where enhanced crush resistance is desired the use of monofilaments may be effective in achieving this end. Useful yarns have from about 1 to about 100 filaments and desirably about 30 filaments. A high filament count for the same overall linear density increases the yarn flexibility, reduces its stiffness and reduces permeability to viscous liquids, i.e., blood.

Multi-ply yarns may be used in the prosthesis of the present invention. Multi-ply yarn is desirable to impart certain properties onto the drawn yarn, such as higher tensile strength. The cold drawn PTFE yarns used in the present invention are desirably drawn at a temperature below the glass transition temperature (Tg) or below the maximum Tg, if the material has multiple Tg's. A suitable temperature range is from about −178 ° C. to about +70° C. The PTFE yarn is desirably drawn at room temperature as long as room temperature is below Tg of the yarn.

Figure 2:
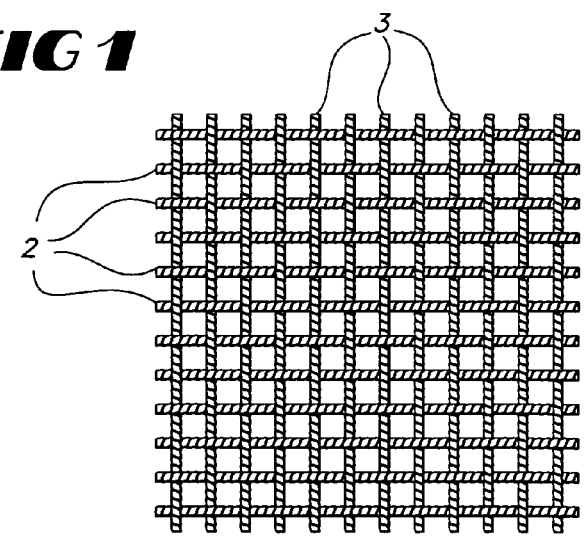
FIG. 2 is a schematic of a conventional weave pattern useful in the present invention.
Figure 3:
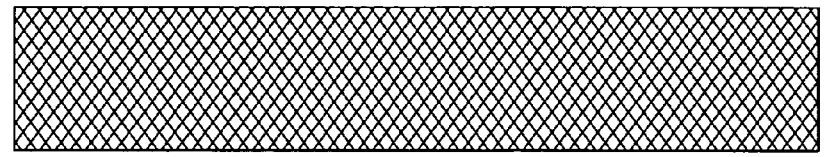
FIG. 3 is a side elevational view of a braided tubular prosthesis useful in the present invention.
Figure 3C:
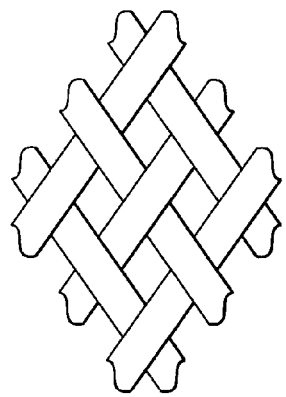
FIG. 3C is a schematic of a hercules braid useful in the present invention.
Figure 3C:
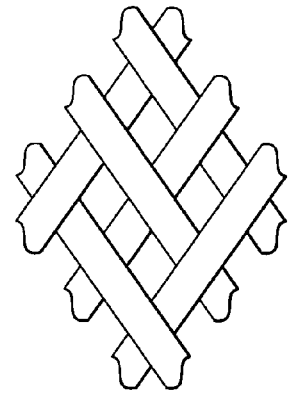
Figure 3C:
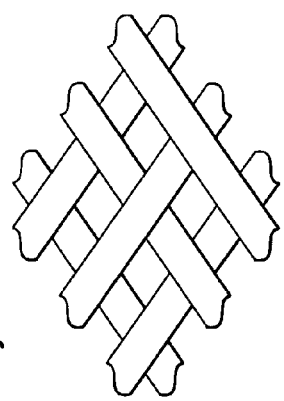

Prostheses made from cold drawn PTFE yarns can have virtually any textile construction, including weaves, knits, braids, filament windings and the like. Referring to the drawings and, in particular to FIGS. 1-2, a woven tubular prosthesis is shown. Any known weave pattern in the art, including, simple weaves, basket weaves, twill weaves, velour weaves and the like may be used. The weave pattern includes warp yarns 2 running along the longitudinal length (L) of the woven product and fill yarns 3 running around the circumference (C) of the product the warp, the fill yarns being at approximately 90 degrees to one another with fabric flowing from the machine in the warp direction.

Braiding may also be used as shown, for example, in FIGS. 3 and 3A-3C. Braiding of yarns includes the interlacing of two yarn systems such that the paths of the yarns are diagonal to the fabric delivery direction, forming either a flat or tubular structure. Useful braids include an interlocking three-dimensional braid and a solid three-dimensional braid. A multi-layered braided structure is defined as a structure formed by braiding wherein the structure has a plurality of distinct and discrete layers. These layers may be bound by interlocking yarns or by adhesive laminates, sewing or the like.

Figure 7:
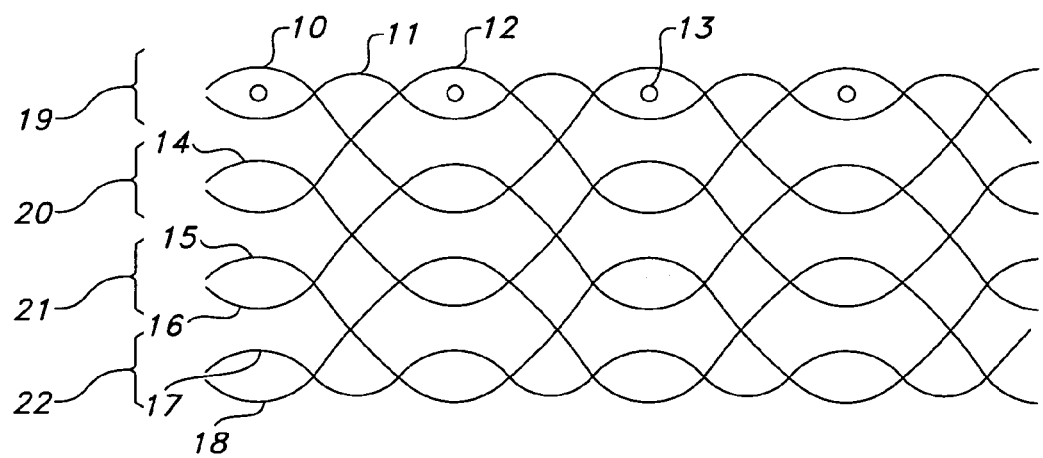
FIG. 7 is a cross-sectional view of a portion of a multi-layered interlocked three-dimensional braided prosthesis formed in accordance with an embodiment of the present invention.

An interlocking three-dimensional braid, as shown in FIG. 7, may be used and is defined as a braided structure having at least two layers, whereby a yarn is interbraided from a first layer into a contiguous second layer to interlock the layers of the multi-layer braid. A braiding machine capable of forming the interlocked three-dimensional braid used to form a prosthesis of the present invention is described in International Patent Publication No. WO 91/10766, which is incorporated herein by reference. Referring to FIG. 7, the prosthesis includes four layers, 19, 20, 21 and 22, with each layer having at least one interlocking yarn from a contiguous layer. The interlocking yarns are braided into the structure so that the yarn forms part of the first layer, as well as being part of the contiguous layer by forming the interlock. Within each layer, a segment of the braid is formed by an interlocking yarn from a contiguous layer, the layers being interbraided together. The interlocking yarns couple the multiple layers together to form a three-dimensional braid. In FIG. 7, the first layer 19 forms the outer layer of the interlocking three-dimensional braided structure. The outer layer is formed from yarn 11 which is exclusively braided into the first layer along with yarn 10 which is interbraided into a second layer which is contiguous with the first layer and yarn 12 which is interbraided from the second layer up into the first layer. Second layer 20 is formed from segments of four yarns 10, 12, 14 and 16 which are interbraided. The next contiguous layer 21 is formed from segments of four yarns 14, 15, 16 and 18 interbraided to form an inner layer in the multilayered structure. Layer 22 is formed in similar fashion, having three yarns 15, 17 and 18 which are interbraided.

Figure 8:
FIG. 8 is a photograph of an enlarged cross-section of a solid three-dimensional braided structure formed in accordance with one embodiment of the present invention.

A solid three-dimensional braided structure, as shown in FIG. 8, may be used and is formed by continuous intertwining of the fibers. Solid three-dimensional braids are homogenous in that all yarns are present throughout the thickness of the braid. Generally, three-dimensional braiding machines used to form this type of solid braid include an array of fiber bobbins held in ring or track configurations. A suitable apparatus for forming a solid three-dimensional braid in accordance with the present invention is disclosed in U.S. Pat. No. 4,719,837. Circumferential motion of the array of the bobbins to form the braid is accomplished by shifting slotted rings containing the fiber holders. Fibers are directed through the thickness of the braid by shifting the holders between the rings. Reversal of the direction of ring and hold motions during the shift segment interlocks the fibers. Since every fiber undergoes a similar motion, all fibers become entwined in the balanced array as illustrated in FIG. 8.

Generally, a braided structure is formed having a braid angle from about 54.5° to about 90° with respect to the longitudinal axis of the braided structure, desirably about 54.5° to about 75°. The yarns of the braid tend to seek equilibrium at a braid angle of about 54.5°, which is the neutral angle for tubular vessels under pressure. Thus, when the braid angle is larger than the neutral angle, when pressure is exerted from within, for example due to fluid flow, the yarns will tend to scissor and decrease the braid angle thereby elongating or stretching the braided structure in order to reach the neutral angle.

Figure 4:
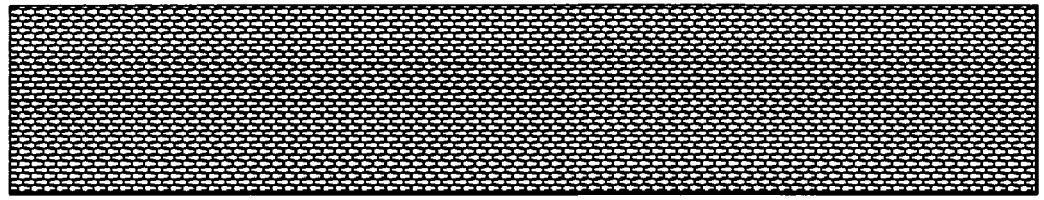
FIG. 4 is a side elevational view of a knitted tubular prosthesis useful in the present invention.
Figure 4A:
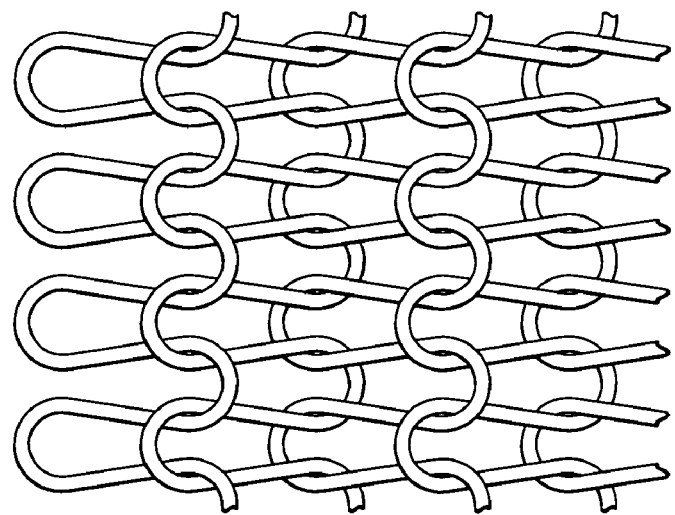
FIG. 4A is an enlarged detail of FIG. 4.
Figure 5:
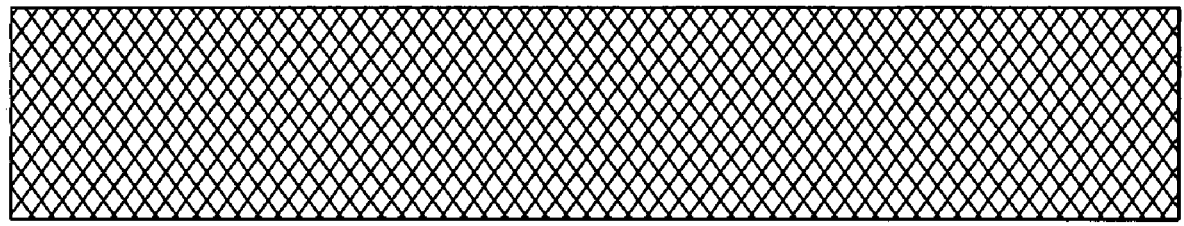
FIG. 5 is a side elevational view of a filament wound tubular prosthesis useful in the present invention.
Figure 5A:
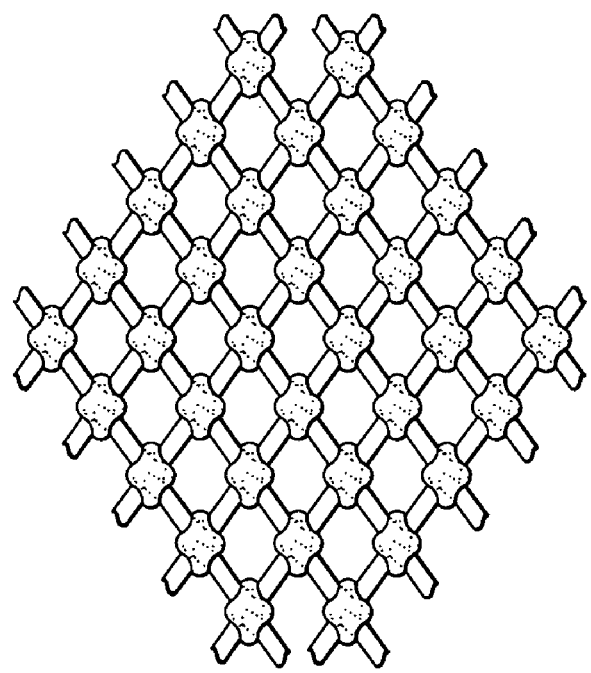
FIG. 5A is an enlarged detail of FIG. 5.

Additionally, knitted prostheses, as shown in FIGS. 4 and 4A, may be used. Knitting involves the interlooping of one yarn system into vertical columns and horizontal rows of loops called wales and courses, respectively, with fabric coming out of the machine in the wale direction. A filament wound prosthesis, as shown in FIGS. 5 and 5A, may also be used where a yarn is transferred from one package to a mandrel to form a prosthesis that is wrapped with the yarn in both directions to provide a biaxial reinforcement.

Generally, tubular textile prostheses are manufactured into a single long tube and cut to a predetermined length. To cut the prosthesis, desirably a laser is used, which cuts and fuses the ends simultaneously. The prosthesis is cleaned, desirably, with sodium dodecyl sulfate and then rinsed with deionized water. The prosthesis is placed over a mandrel and heat set to precisely set the diameter and to remove any creases or wrinkles. Typically heat conditioning is carried out at a temperature range from about 125° C. to about 225° C. using a convection oven for a time of 20 minutes. Any known means for heating the structure may be used. The prosthesis may then be attached to a stent fixation device and assembled into a catheter delivery system, or alternatively surgically implanted.

Figure 6:
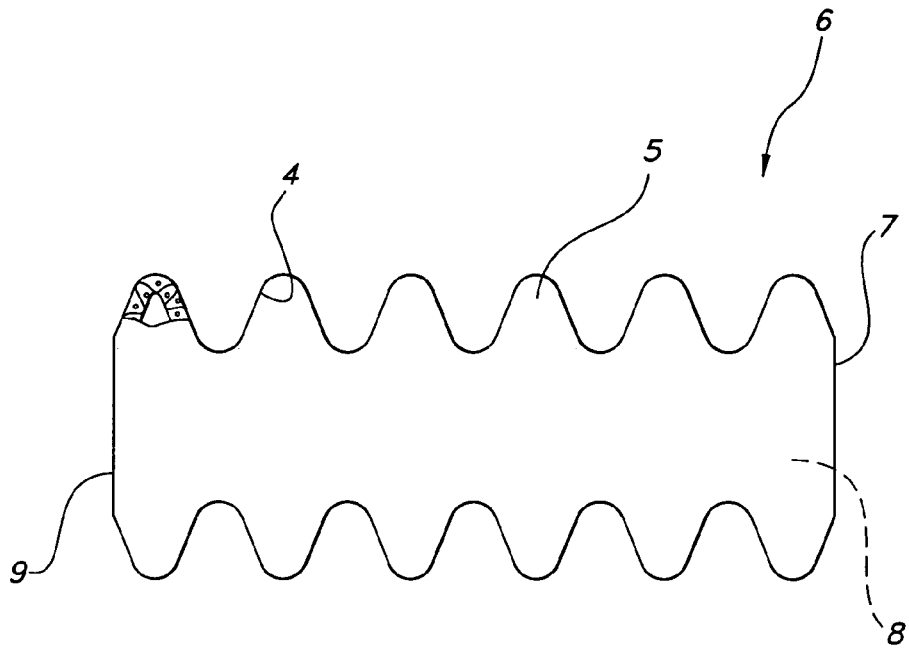
FIG. 6 shows schematically, in partial section, a prosthesis of the present invention with a series of wave-like crimps.

Once deployed, the inventive prosthesis desirably maintains its longitudinal flexibility and returns to its tubular open lumen configuration so that the lumen remains open allowing the passage of blood. As shown in FIG. 6, crimps 4 may optionally be employed with the present invention to permit such longitudinal flexibility and structural integrity without increasing the graft thickness as measured by both fabric wall thickness and as measured between the peak-to-peak amplitude of the wave-like pattern of crimps. The prosthesis 6 includes a generally tubular body 5 having opposing ends 7 and 9 which define therebetween an open lumen 8 which permits passage of blood once the graft 6 is implanted in the blood vessel.

Figure 9:
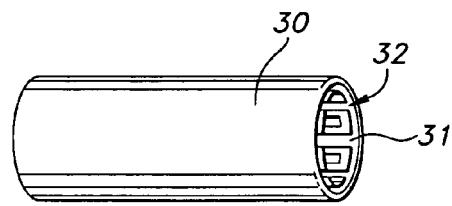
FIG. 9 is a perspective showing of a prosthesis and a stent-graft composite of the present invention with a stent incorporated therein.
Figure 10:
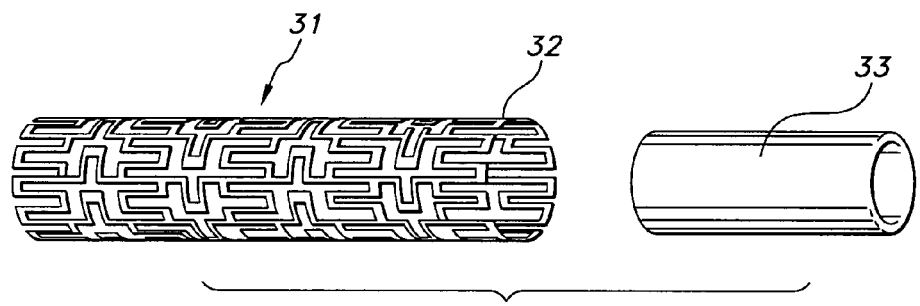
FIG. 10 is a perspective showing a stent with an inner graft liner.
Figure 11:
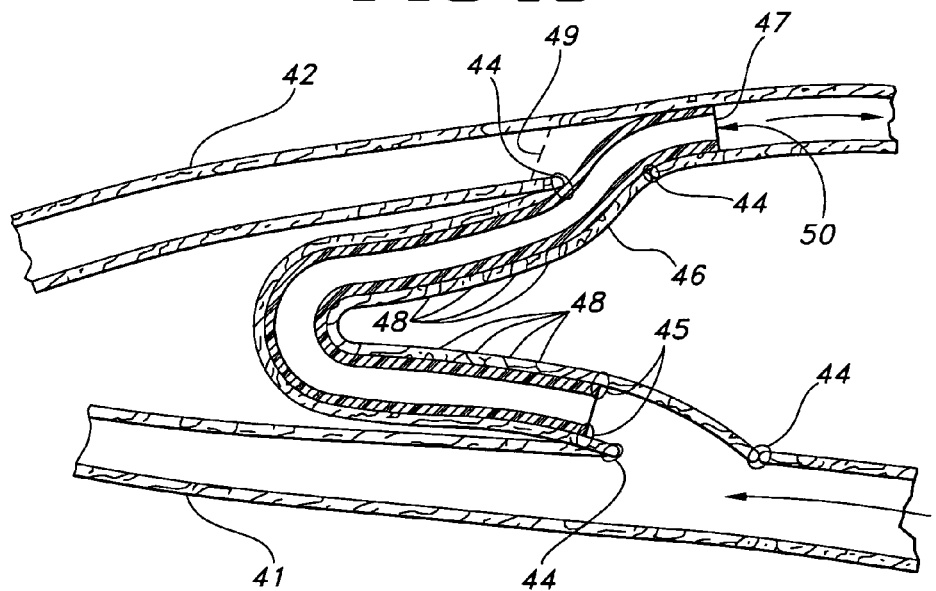
FIG. 11 describes a cross section of an arteriovenous vascular graft.

As shown in FIGS. 9 and 10, a stent may be incorporated in the prosthesis to help secure the prosthesis to the host lumen. In that way, both the prosthesis 30 and the stent 31 can be simultaneously and controllably expanded to the desired diameter or until the stent/graft composite 32 substantially conforms to the diameter of the host lumen. Any suitable means of attaching the stent 31 to the expandable prosthesis 30, such as hooks, catches, sutures or other similar means may be used. Incorporating the stent 31 between layers of fabric or graft walls 30 and 31 to form a composite structure is also contemplated. Additionally, the stent 31 may include similar means capable of anchoring the prosthesis in place in the host lumen. This is often accomplished by expanding the stent-graft structure such that sufficient radial pressure against the luminal surface of the vessel provides for anchoring. Alternatively or in addition to anchoring by using a sufficiently tight radial fit, various barbs or hooks may be used to secure the prosthesis in place in the host vessel.

The prostheses of the present invention may be coated with a bio-absorbable coating, such as collagen, albumin, elastin and the like. Such coatings are known in the art and are desirable in vascular and endovascular graft applications to seal the graft and thereby prevent blood loss in the early stages of implantation. Other coatings which may be used include those disclosed in U.S. Pat. No. 5,851,229, which is incorporated herein. The '229 patent discloses a sealant composition that includes at least two polysaccharides in combination to form a hydrogel or solgel. Sealant compositions may include a bioactive agent and or be cross-linked subsequent to the application of these compositions to the substrate surface. Additionally, U.S. Pat. No. 5,209,776, incorporated herein, discloses a composition that includes a first protein component that is preferably collagen and a second protein-supporting component that can be a proteoglycan, a saccharide or a polyalcohol.

Desirably, the prostheses of the present invention are impregnated with a leak resistant material.

The prosthesis of the present invention includes cold drawn PTFE yarn. Other yarns which may be incorporated therein include, but are not limited to, polyester materials such as polyethyleneterepthalate (PET), poly(glycolic acid), poly (lactic acid), polydioxanoes, polyoxalates, poly(alpha esters), polycarbonates, polyanhydrides, polyacetals, polycaprolactones, poly(orthoesters), polyamino acids, polyurethanes, polyiminocarbonates, polyamindes, poly(alkyl cyanoacrylates), sebacic acid, polyethylene glycol, polyphosphazene, bis(p-carboxyphenoxy)propane, bis(p-carboxyphenoxy)methane and copolymers and mixtures thereof, provided that these materials can be formed into a fiber suitable for use with the textile manufacturing apparatus being used. A bioabsorbable yarn may be used in either a single layer, in several different layers, or as several yarns within a textile structure to form a prosthesis having an initial porosity different from the porosity once the bioabsorbable material has been absorbed into the body.

Axial yarns are added in some cases to limit a textile structure from stretching beyond a desired amount, and thereby significantly reducing the potential for scissoring action of the yarns. This scissoring or shearing action is detrimental to the body's healing process. The scissoring action of the strands tends to prevent the tissue and blood vessels from infiltrating the pores of the structure. Additionally, an axial yarn may be dyed and inserted into the textile structure subsequent to or during the braiding process. A dyed axial yarn positioned in the outer surface of the prosthesis aids the surgeon during implantation to indicate whether the prosthesis is straight and not twisted during the procedure.

The prosthesis may include a radiopaque guideline or marker to provide means for viewing the implanted prosthesis fluoroscopically. The marker may extend the length of the prosthesis. Other patterns for markers may also be employed. Radiopaque markers assist the surgeon to visualize the prosthesis both during and after implantation. The marker helps show the surgeon that the prosthesis is properly positioned. Also, it will indicate whether the prosthesis has dilated or collapsed after implantation.

Figure 12:
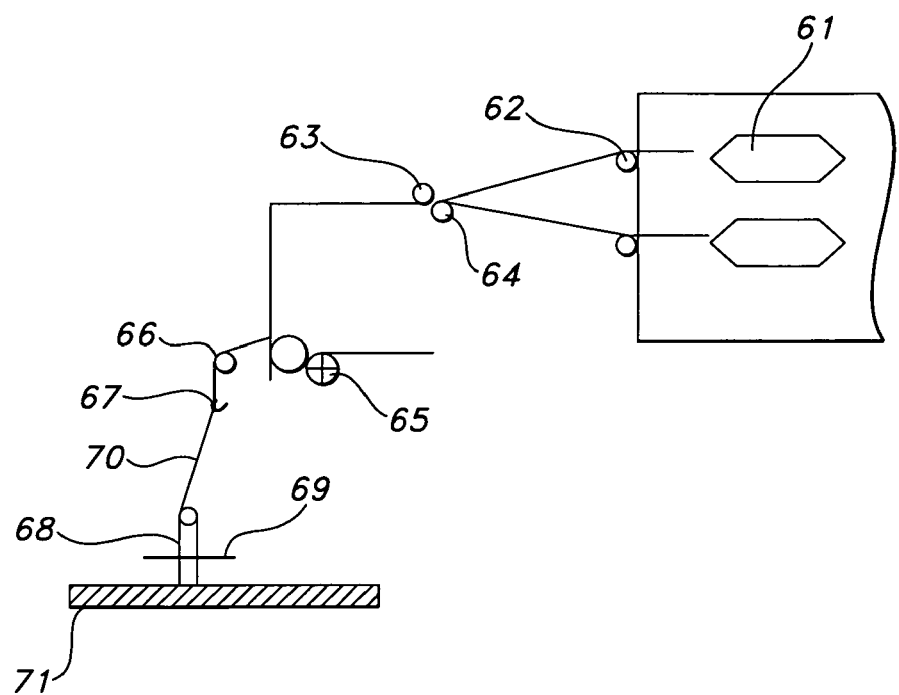
FIG. 12 is a schematic view of a cold drawing apparatus.

The prosthesis of the present invention incorporates cold drawn PTFE yarn therein as more particularly described in commonly owned patent application, U.S. patent application Ser. No. 10/133,526, entitled "Cold Drawing Process of Polymeric Yarns Suitable For Use in Implantable Medical Devices", filed Apr. 25, 2002, now U.S. Pat. No. 6,763,599, and incorporated herein by reference. FIG. 12 is a schematic view of the apparatus used for a method of cold drawing PTFE yarns. The apparatus of FIG. 12 includes package creel 61, creel roller guide 63, tension roller 64, second roller 65, separator roller 66, pigtail guide 67, spindle 68, ring and traveler 69, yarn 70 and frame 71, interrelated as shown.

As illustrated in FIG. 12, the cold drawing apparatus desirably is equipped with a package creel 61 which holds the undrawn yarn. The yarn is fed through creel roller guide 62 and then drawn over first roller guide 63 that spins about its axis at a first speed and second roller 65, which turns about its axis at a speed faster than the speed of the first roller to draw the yarn to a desired denier and to enhance filament orientation. Creel roller guide 62 is freely rotatable and the speed of first roller guide 63 and second roller 65 are pre-adjustable.

The properties of the drawn yarn can be tailored to meet the requirements of a particular use. Properties of the drawn yarn may be altered, for instance, by varying the draw ratio, twisting amount and adding multiple yarns to produce a multi-ply finished yarn. The draw ratio indicates the ratio of the speed of the second roller 65 turning about its axis compared to first roller 63 turning about its axis. Useful draw ratios are from about 1.05 to about 1.50. A draw ratio of higher than 1.50 may result in breakage of the yarn. The draw ratio is based on the desired tension strength, orientation and linear density of the yarn. A higher draw ratio will result in a larger reduction in the linear density of the yarn.

As shown in FIG. 12, yarn 70 leaves pigtail guide 67 and is guided onto spindle 68 and twisted by ring and traveler 69, which increases the strength of the yarn and prevent the filaments of the yarn from fraying. PTFE yarn that is not twisted may fray and separate due to the electrostatic forces present on the filaments of the yarn. Useful twisting rates are from about 0.5 turns per inch (tpi) to about 20 turns per inch and more desirably from about 0.5 tpi to about 5 turns per inch. An anti-static agent may be added to the PTFE yarn to minimize static charges that may accumulate on the yarns. The cold drawn PTFE yarn desirably has a linear density of about 40 to about 300 denier. Desirably, the cold drawn PTFE yarn has a linear density from about 216-262 denier with a standard deviation from about 0.5 to about 10 denier.

Desirably, the cold drawn PTFE yarn has a tenacity from about 0.06 to about 0.45 grams/denier. Desirably, the standard deviation the linear density of the cold drawn PTFE yarn is from about 0.2% to about 0.8%. Cold drawn PTFE yarns having a standard deviation in linear density of about 0.5 denier to about 2.0 denier are also useful.

The following examples are presented for purposes of illustration only and are not intended to limit the scope of the invention. For all examples, the prosthesis may be of a straight, bifurcated or otherwise designed configuration.

EXAMPLE 1

Woven Construction

A prosthesis is flat woven on an electric jacquard loom in a tubular configuration. A 1/1 plain, tubular weave is used with a warp yarn of 225 denier, 30 filament cold drawn PTFE yarn. A 225 denier, 30 filament cold drawn PTFE yarn is used with 160 warp ends per inch per layer and 120 pick yarns per inch per layer.

After weaving into a tubular prosthesis, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles.

EXAMPLE 2

Woven Construction

A graft-stent composite, in accordance with the present invention, is formed from a plain weave tubular fabric having a warp yarn of 225 denier, 30 filament cold drawn PTFE yarn and weft yarn of 225 denier, 30 filament cold drawn PTFE yarn. The ends per square inch are 188 per layer while the picks per inch are 88 per layer. The fabric so formed has a wall thickness of approximately 0.12 mm or less.

After weaving into a tubular prosthesis, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles.

The prosthesis is optionally be crimped to impart longitudinal compliance and radial support. Crimp patterns shown in FIG. 6 include a series of wave-like crimps therealong. Crimps may be imparted on a finer pitch as the relatively thin fabric would not impede such fine pitch crimping.

A stent is inserted into the graft (endoprosthesis) to form a stent/graft composite. To secure the stent, it is sutured into place or inserted into a cuff of the graft. Either two stents are inserted at each end of the graft or one stent is inserted at one end. Alternatively, one stent or a series of connected stents may be inserted throughout the length of the graft. Alternatively the stent may be sandwiched between two grafts.

EXAMPLE 3

Braided Construction

A regular twill braid is used to produce a tubular prosthesis. The warp yarns and fill yarns are constructed of a 225 denier, 30 filament cold drawn PTFE yarns. A prosthesis is braided using 192 bobbins and a 55 degree helix angle.

After braiding into a tubular prosthesis, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles.

EXAMPLE 4

Interlocked 3-D Braided Construction

A tubular prosthesis is formed from an interlocked three-dimensional, multi-layered braided structure, as shown in FIG. 7. The prosthesis is preferably braided on a mandrel at a braid angle of 54.5 degrees. The prosthesis includes four interlocked layers made 225 denier, 30 filament cold drawn PTFE yarns having 192 bobbins (bobbins refer to the number of carriers within the braiding machine).

After braiding into a tubular prosthesis, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles.

EXAMPLE 5

Solid 3-D Braided Construction

A tubular prosthesis is formed from a solid three-dimensional braided structure, as shown in FIG. 8, having six strands forming three plies which are interbraided through the thickness of the braid. The prosthesis is formed from 225 denier, 30 filament cold drawn PTFE yarns, which are placed on each of the 192 bobbins on the braiding machine.

After braiding, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles. The prosthesis is attached to a stent fixation device and assembled into a catheter delivery system, or alternatively surgically implanted.

EXAMPLE 6

Weft Knitted Construction

A tubular jersey weft knit is used with a three-ply, 225 denier, 30 filament cold drawn PTFE yarns with 30 wales per inch per layer and 40 courses per inch per layer. A warp knit construction may also be used. For example, instead of a tubular jersey weft knit construction, a tubular double tri-cotton warp knit construction with similar stitched density to the tubular jersey weft knit can be used.

After knitting, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles. The prosthesis is attached to a stent fixation device and assembled into a catheter delivery system, or alternatively surgically implanted.

EXAMPLE 7

Filament Wound Construction

A one-ply, 225 denier, 30 filament cold drawn PTFE yarn is filament wound onto a mandrel of known diameter. The helix angle achieved is about 55 degrees. The mandrel is wrapped with the yarn in both directions to provide biaxial reinforcement. To hold the yarns in place, they are passed through a solution of solvated polyurethane elastomer, such a BIOMARK® solution, sold by Johnson & Johnson. The solvent is removed, causing the polyurethane to dry and glue the yarns together.

After winding, the prosthesis is cut to a desired length, desirably with a laser to cut and fuse the ends simultaneously. The prosthesis is cleaned with sodium dodecyl sulfate and then rinsed with deionized water. The prosthesis is placed over a mandrel and heat set to precisely set the diameter and to remove any creases or wrinkles. The prosthesis is attached to a stent fixation device and assembled into a catheter delivery system, or alternatively surgically implanted.

The preferred embodiments having been thus described, it will now be evident to those skilled in the art that further variation thereto may be contemplated. Such variations are not to be regarded as a departure from the invention, the true scope of the invention being set forth in the claims appended hereto.

What is claimed:

1. An implantable textile prosthesis comprising:
a hollow tubular textile construction of a biocompatible yarn, wherein said yarn comprises a cold drawn PTFE yarn having a substantially uniform denier with a standard deviation of less than about 0.8% and a tenacity from 0.36 to 0.45 grams/denier and high molecular orientation fabric.

2. The prosthesis of claim 1, wherein said textile construction is selected from the group consisting of weaves, knits, braids, filament windings, spun windings and combinations thereof.

3. The prosthesis of claim 1, wherein said prosthesis is a tubular vascular or endovascular graft.

4. The prosthesis of claim 1, wherein said prosthesis further includes a coating.

5. The prosthesis of claim 1, wherein said prosthesis includes a radially deformable support component.

6. The prosthesis of claim 5, wherein said support component is a radially deformable stent.

7. The prosthesis of claim 1, wherein said yarn has a linear density of at least about 40 denier; and further wherein said yarn has a linear density of no more than about 400 denier.

8. The prosthesis of claim 1, wherein said yarn is twisted with at least about 1 twist per inch; and further wherein said yarn is twisted with no more than about 10 twists per inch.

9. The prosthesis of claim 1, wherein said yarn includes an anti-static lubricant.

10. The prosthesis of claim 1, wherein said yarn is a room temperature, cold drawn yarn.

11. The prosthesis of claim 1, wherein said prosthesis is impregnated with a leak resistant material.

12. The prosthesis of claim 1, wherein said prosthesis includes an axial yarn to control longitudinal extension thereof.

13. The prosthesis of claim 1, wherein said cold drawn PTFE yarn has a substantially uniform denier with a standard deviation from about 0.2% to about 0.8%.

14. The prosthesis of claim 1, wherein said cold drawn PTFE yarn has a substantially uniform denier with a standard deviation from about 0.5 to about 10 denier.

15. The prosthesis of claim 1, wherein said cold drawn PTFE yarn was cold drawn at a draw ratio of about 1.05 to about 1.50 and at room temperature.

16. The prosthesis of claim 1, wherein said cold drawn PTFE yarn is selected from the group consisting of a flat yarn, a twisted yarn, a textured yarn, a pre-shrunk yarn and combinations thereof.

17. The prosthesis of claim 1, wherein said cold drawn PTFE yarn is selected from he group consisting of a multifilament yarn, a monofilament yarn, a spun type yarn and combinations thereof.

18. An implantable textile prosthesis comprising:
a hollow tubular textile construction of a biocompatible yarn, wherein said yarn comprises a PTFE yarn having a linear density from about 40 denier to about 400 denier and a tenacity from 0.36 to 0.45 grams/denier.

19. An implantable textile prosthesis comprising:
a hollow tubular textile construction of a biocompatible yarn, wherein said yarn comprises a cold drawn PTFE yarn comprising a weave pattern selected from the group consisting of simple weaves, plain weaves, basket weaves, twill weaves and velour weaves and having a substantially uniform denier with a standard deviation of less than about 0.8% and a tenacity from 0.36 to 0.45 grams/denier and high molecular orientation fabric.

20. The implantable textile prosthesis of claim 19 wherein said weave pattern comprises a longitudinal length and a circumference, said weave pattern includes warp yarns running along the longitudinal length of the weave pattern and fill yarns running around the circumference of the weave pattern, the fill yarns being approximately 90 degrees to one another.

* * * * *